(12) United States Patent
Tange et al.

(10) Patent No.: US 8,486,036 B2
(45) Date of Patent: Jul. 16, 2013

(54) ABSORBENT ARTICLE

(75) Inventors: Satoru Tange, Kagawa (JP); Toshio Inoue, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 705 days.

(21) Appl. No.: 12/449,319

(22) PCT Filed: Dec. 14, 2007

(86) PCT No.: PCT/JP2007/074093
§ 371 (c)(1),
(2), (4) Date: Jan. 15, 2010

(87) PCT Pub. No.: WO2008/096504
PCT Pub. Date: Aug. 14, 2008

(65) Prior Publication Data
US 2010/0168703 A1  Jul. 1, 2010

(30) Foreign Application Priority Data
Feb. 2, 2007 (JP) .................................. 2007-024791

(51) Int. Cl.
*A61F 13/15* (2006.01)
*A61F 13/20* (2006.01)

(52) U.S. Cl.
USPC ................. 604/385.01; 604/367; 604/360

(58) Field of Classification Search
USPC ............... 604/358, 359, 362, 385.01, 367
See application file for complete search history.

(56) References Cited

U.S. PATENT DOCUMENTS

| 3,860,003 | A | * | 1/1975 | Buell ..................... 604/385.25 |
| 5,643,588 | A | * | 7/1997 | Roe et al. .................. 424/402 |
| 2001/0049512 | A1 | | 12/2001 | Kawamura et al. |
| 2003/0135189 | A1 | | 7/2003 | Umebayashi |
| 2007/0032766 | A1 | * | 2/2007 | Liu et al. ................... 604/361 |

FOREIGN PATENT DOCUMENTS

| JP | 03-090602 | 4/1991 |
| JP | 2001-478 | 1/2001 |
| JP | 2001-327534 | 11/2001 |
| JP | 2005-237768 | 9/2005 |
| JP | 2006-181193 | 7/2006 |

* cited by examiner

*Primary Examiner* — Michele M Kidwell
(74) *Attorney, Agent, or Firm* — Brinks Hofer Gilson & Lione (57) ABSTRACT

The present invention aims to provide an absorbent article incorporated with a functional sheet without any anxiety that the wearer's skin might be contaminated even though the article is partially colored.

In an absorbent article 1a comprising a sheet assembly 10, a functional sheet 51 having a size smaller than that of the sheet assembly 10, and a bodily fluid-absorbent structure 30 wherein the functional sheet 51 and the bodily fluid-absorbent structure 30 are attached to the sheet assembly 10, the functional sheet 51 is put flat with and bonded to the sheet assembly 10 so as to be kept in contact with the wearer's skin and an externally visible colored zone 4 is provided between the functional sheet 51 and the sheet assembly 10.

8 Claims, 7 Drawing Sheets

Impacted surface (Magnification: ×19)

FIG. 7

Opposite surface (magnification: ×19)

FIG. 8

(Magnification: ×1000)

FIG. 9

(Magnification: ×4000)

ABSORBENT ARTICLE

RELATED APPLICATIONS

The present application is a 35 U.S.C. §371 national stage filing of International Patent Application No. PCT/JP2007/074093, filed Dec. 14, 2007, to which priority is claimed under 35 U.S.C. §120 and through which priority is claimed under 35 U.S.C. §119 to Japanese Priority Patent Application No. 2007-24791, filed Feb. 2, 2007.

TECHNICAL FIELD

The present invention relates to an absorbent article including a functional sheet.

RELATED ART

It is well known to incorporate a functional sheet impregnated with antimicrobial agent or deodorant into the absorbent article such as disposable diaper or sanitary napkin and thereby to add the absorbent article with an additional function. The absorbent article according to this technique has sometimes been partially colored, for example, by printing in order to camouflage any intrinsic color of the antimicrobial agent or the other functional additives or in order to facilitate the article to be distinguished from the similar article without the functional sheet incorporated thereinto.

PATENT DOCUMENT 1 discloses the absorbent article provided in a region on the side thereof facing the wearer's skin extending outward beyond the peripheral edge of the absorbent core with a plurality of spots depressed in the thickness direction of this region wherein an appropriate quantity of ink is transferred into each of these depressed spots to form a printed pattern.

PATENT DOCUMENT 1: Japanese Patent Application Laid-Open Publication No. 2006-181193 (claim 1, FIG. 1)

DISCLOSURE OF THE INVENTION

Problem to be Solved by the Invention

In the case of the absorbent article disclosed in PATENT DOCUMENT 1, the printed pattern serves to improve the leak-barrier effect and to give the wearer a feeling of assurance by making the wearer recognize such improvement of the leak-barrier effect.

However, it is apprehended that the printed pattern of ink provided directly on the side of the absorbent article facing the wearer's skin might fall away from the article and the wearer's skin might be contaminated therewith. Thus, there is a need for further improvement.

In view of the problem as has been described above which has been left behind unsolved by the prior art, it is a principal object of the present invention to provide an absorbent article incorporated with a functional sheet without any anxiety that the wearer's skin might be contaminated even though the article is partially colored.

Measure to Solve the Problem

The object set forth above is achieved, according to the present invention, by an improvement in the absorbent article comprising a sheet assembly, a functional sheet having a size smaller than that of the sheet assembly, and a bodily fluid-absorbent structure wherein the functional sheet and the bodily fluid-absorbent structure are attached to the sheet assembly.

The improvement according to the present invention is characterized in that the functional sheet is put flat with and bonded to the sheet assembly so as be kept in contact with the wearer's skin and an externally visible colored zone is provided between the functional sheet and the sheet assembly.

According to one preferred embodiment of the present invention, the functional sheet is bonded to the sheet assembly by the intermediary of an adhesive region, the adhesive region is provided so as to be spaced inward from an outer peripheral edge of the functional sheet, and the colored zone is provided in a same region as the adhesive region or within the adhesive region.

According to another preferred embodiment of the present invention, the colored zone is formed by at least one of ink with which the functional sheet is printed, ink with which the sheet assembly is printed, and hot melt adhesive used to bond the functional sheet to the sheet assembly and containing appropriate pigment.

According to still another preferred embodiment of the present invention, the bodily fluid-absorbent structure includes a liquid-absorbent material at least containing fluff pulp and the colored zone is provided in a region of the sheet assembly in which the liquid-absorbent material is not present.

Effect of the Invention

The absorbent article according to the present invention includes the external visible colored zone between the sheet assembly and the functional sheet. In consequence, the colored zone is covered with the functional sheet to prevent the wearer's skin from being contaminated with ink or the other coloring material.

The colored zone may be provided in the same region as the adhesive region or within the adhesive region to prevent, further reliably, the colored zone from coming in contact with the wearer's skin The colored zone may be provided in the region of the sheet assembly in which the bodily fluid-absorbent material including fluff pulp is not present to improve the visibility of the colored zone since the colored zone is not masked by the bodily fluid-absorbent material including fluff pulp.

BRIEF DESCRIPTION OF THE DRAWINGS

[FIG. 1]
[FIG. 2]
[FIG. 3]
[FIG. 4]
[FIG. 5]
[FIG. 6]

[FIG. 7]

[FIG. 8]

[FIG. 9]

IDENTIFICATION OF REFERENCE NUMERALS USED IN THE DRAWINGS

| | |
|---|---|
| 1 | diaper (absorbent article) |
| 4 | colored zone |
| 10 | sheet assembly |
| 30 | bodily fluid-absorbent structure |
| 31 | liquid-absorbent material |
| 51 | sweat-absorbent sheet |
| 57 | hot melt adhesive |
| 58 | outer peripheral edge |
| 59 | ink |
| 61 | adhesive region |

DETAILED DESCRIPTION OF THE PREFERRED EMBODIMENTS

Details of the present invention will be described hereinafter on the basis of a disposable diaper 1, one of typical examples of the invention, in reference to the accompanying drawings wherein the diaper 1 includes an antimicrobial sweat-absorbent sheet 51 as the functional sheet.

Figure 1:
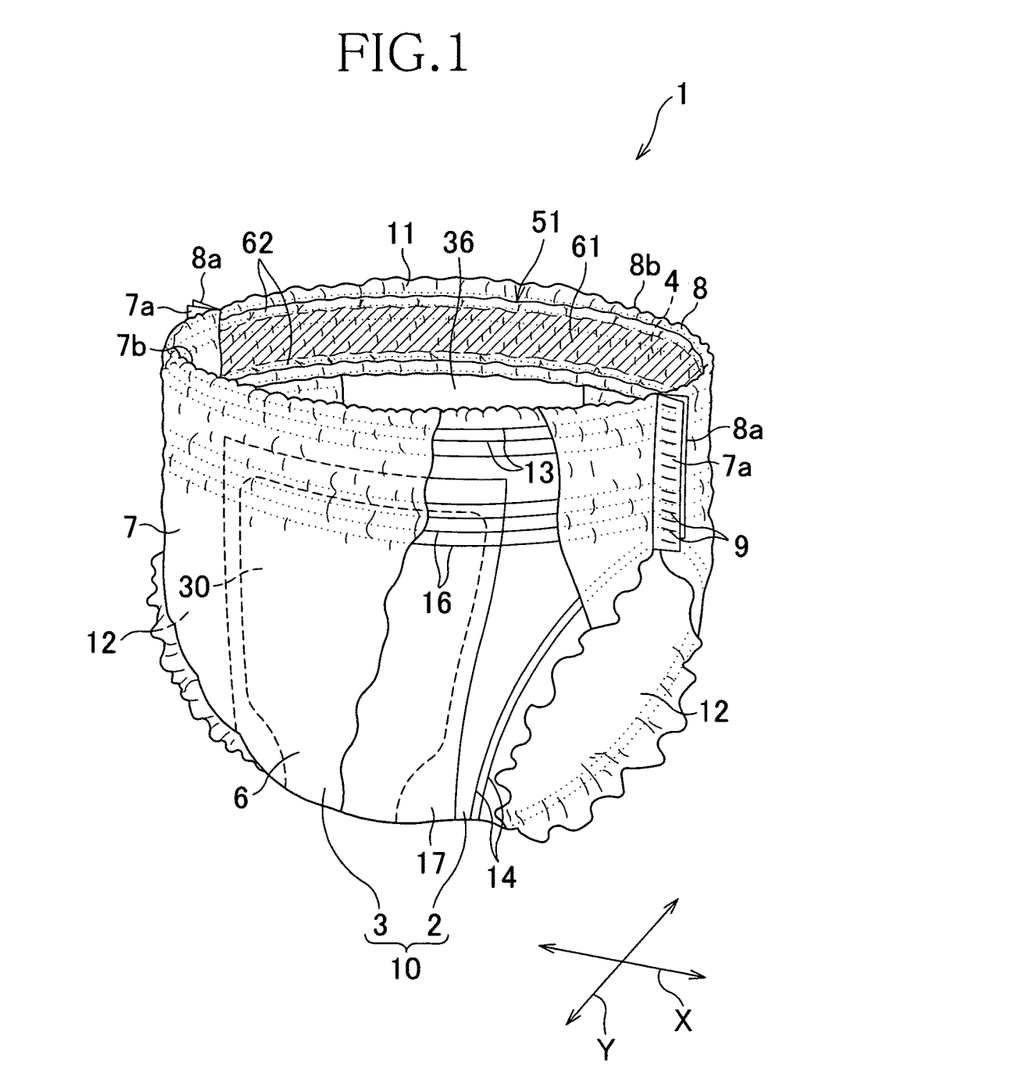
FIG. 1 is a partially cutaway perspective view of the diaper.

FIG. 1 is a partially cutaway perspective view of the disposable diaper 1 according to the invention. The diaper 1 comprises a sheet assembly 10 including a top-sheet 2, a back-sheet 3 and a leak-barrier sheet 17 as primary components, a sweat-absorbent sheet 51 of a size smaller than the sheet assembly 10 and a bodily fluid-absorbent structure 30.

The top-sheet 2 adapted to be kept in contact with diaper wearer's skin is liquid-pervious and air-permeable while the back-sheet 3 serving as exterior material is liquid-impervious but air-permeable. These top- and back-sheets 2, 3 are put flat together and partially bonded to each other by means of hot melt adhesive (not shown) to present a pants-like shape. The pants-type diaper 1 formed in this manner has a crotch region 6 adapted to face the wearer's crotch region, a front waist region 7 extending forward from the crotch region 6 and a rear waist region 8 extending rearward from the crotch region 6. Specifically, the front and rear waist regions 7, 8 respectively have transversely opposite lateral edges 7a, 7a and 8a, 8a along which the front and rear waist regions 7, 8 are put flat and fusion bonded together at bonding short bars 9 intermittently arranged in a vertical direction as viewed in FIG. 1. Thereupon, a waist-opening 11 and a pair of leg-openings 12 are formed.

The leak-barrier sheet 17 is liquid-impervious and sandwiched between the top-sheet 2 and the back-sheet 3 so as to extend across the crotch region 6 into the front waist region 7 and the rear waist region 8. As indicated by a dashed line, the bodily fluid absorbent structure 30 is attached to an inner side (i.e., the side facing the wearer's skin) of the top-sheet 2. In the vicinity of the waist-opening 11, the sweat-absorbent sheet 51 having an externally visible colored zone 4 is bonded to the sheet assembly 10 of the diaper 1 in the rear waist region 8 in a manner that the sweat-absorbent sheet 51 may be kept in contact with the wearer's skin. Referring to FIG. 1, the colored zone 4 is provided on the rear surface of the sweat-absorbent sheet 51 and the range in which the colored zone 4 externally visible is indicated as a shaded region.

In the vicinity of a peripheral edge of the waist-opening 11, a plurality of waist-surrounding elastic members 13 extending along the peripheral edge of the waist-opening 11 are sandwiched between the top-sheet 2 and the back-sheet 3 and bonded under tension to at least one of these top- and back-sheets 2, 3. In the vicinity of respective peripheral edges of the leg-openings 12, a plurality of leg-surrounding elastic members 14 extending in parallel to the respective peripheral edges of the leg-openings 12 are sandwiched between the top-sheet 2 and the back-sheet 3 and bonded under tension to at least one of these top- and back-sheets 2, 3. In addition to these elastic members 13, 14, a plurality of auxiliary waist-surrounding elastic members 16 circumferentially extending in parallel to the waist-surrounding elastic members 13 are provided between front and rear edges 7b, 8b of the peripheral edge of the waist-opening 11 and the peripheral edges of the respective leg-openings 12. These auxiliary waist-surrounding elastic members 16 are also sandwiched between the top-sheet 2 and the back-sheet 3 and bonded under tension to at least one of these top- and back-sheets 2, 3.

Figure 2:
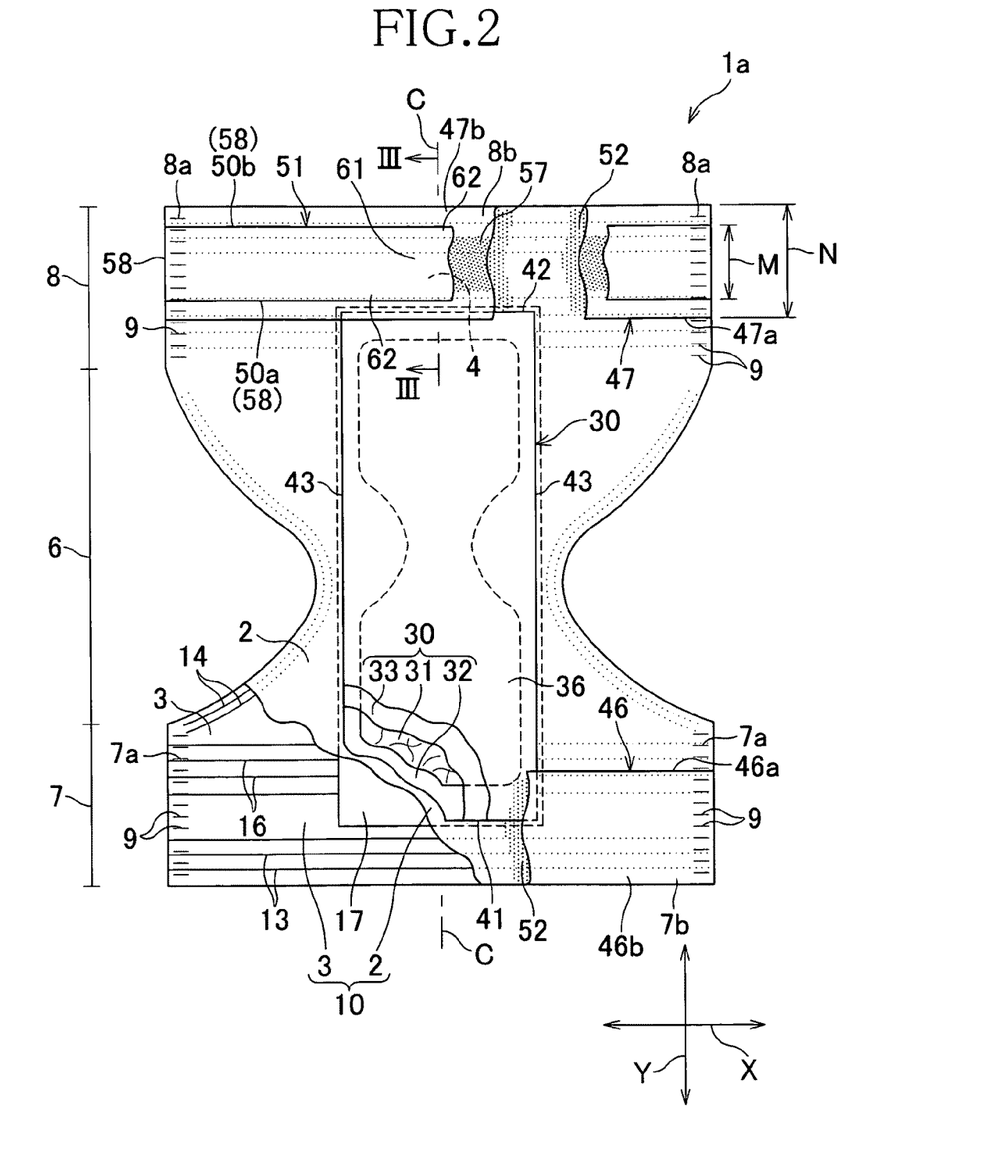
FIG. 2 is a plan view showing the diaper of FIG. 1 as the front and rear waist regions have been disconnected from each other and the diaper as a whole has been flatly developed.

FIG. 2 is a partially cutaway plan view showing the diaper 1 of FIG. 1 as the front and rear waist regions 7, 8 have been torn apart from each other along the arrays of bonding short bars 9 and the diaper 1 as a whole has been developed in a transverse direction indicated by a double-headed arrow X as well as in a front-back direction orthogonal to the transverse direction X and indicated by a double-headed arrow Y. For a viewer of FIG. 2, the top-sheet 2, i.e., the side of the diaper 1a facing the wearer's skin, is shown on the near side.

The sheet assembly 10 including the top-sheet 2, the back-sheet 3 and the leak-barrier sheet 17 as the primary components has a contour in the crotch region 6 which curves inwardly of the diaper 1a and thereby presents an hourglass-like shape as a whole. The top-sheet 2 constituting the sheet assembly 10 is provided in a central region with the bodily fluid-absorbent structure 30 covered with a liquid-absorbent top-sheet 36. The bodily fluid-absorbent structure 30 extends across the crotch region 6 into the front waist region 7 as well as into the rear waist region 8 and has a shape symmetric about a longitudinal center line C-C substantially bisecting a transverse dimension of the diaper 1a.

The bodily fluid-absorbent structure 30 is formed by liquid-absorbent material 31 such as fluff pulp or a mixture of fluff pulp and super-absorbent polymer particles sandwiched between a sheet of tissue paper 32 and a sheet of tissue paper and further covered with the previously described liquid-pervious top-sheet 36 directly facing the wearer's skin. The sheets of tissue paper 32, 33 and the top-sheet 36 are substantially same in shape as well as in size and put flat together along transversely opposite lateral edges 43, 43 extending in the front-back direction, front and rear ends 41, 42 extending in the transverse direction of the bodily liquid-absorbent structure 30. It should be appreciated that the top-sheet 2 is sandwiched between the bodily fluid-absorbent structure 30 and the leak-barrier sheet 17 in the case of the illustrated embodiment.

In the front and rear waist regions 7, 8 of the diaper 1a, the front edge 7b and the rear edge 8b cooperating to define the peripheral edge of the waist-opening 11 in FIG. 1 extend in the transverse direction in FIG. 2.

The back-sheet 3 is folded back along the front edge 7b and the rear edge 8b onto the side of the diaper 1a on which the bodily fluid-absorbent structure 30 is attached. The portion of the back-sheet 3 folded back along the front edge 7b will be referred to hereinafter as a front turnback 46 and the portion of the back-sheet 3 folded back along the rear edge 8b will be referred to hereinafter as a rear turnback 47.

A front lower edge 46a defined by a distal end of the front turnback 46 overlaps the front end 41 of the bodily fluid-absorbent structure 30. A rear lower edge 47a defined by a distal end of the rear turnback 47 also overlaps the rear end 42 of the bodily fluid-absorbent structure 30 but short of the liquid-absorbent material 31.

Referring to FIG. 2, the front turnback 46 and the rear turnback 47 are bonded to the top-sheet 2 by means of adhesive 52 such as hot melt adhesive. The front turnback 46 and the rear turnback 47 are formed by the liquid-impervious back-sheet 3 and therefore it is not apprehended that a quantity of bodily fluids once having been absorbed by the bodily fluid-absorbent structure 30 might seep out from the bodily fluid-absorbent structure 30 in the front and rear waist regions 7, 8 and come in contact with the wearer's skin.

The sweat-absorbent sheet 51 is substantially rectangular is bonded to the side of the rear turnback 47 facing the wearer's skin by the intermediary of an adhesive region 61 coated with hot melt adhesive 57 so that the sweat-absorbent sheet 51 may be kept in contact with the wearer's skin. The hot melt adhesive 57 is applied in dot-, stripe- or spiral-pattern. Between the sweat-absorbent sheet 51 and the rear turnback 47, there is provided the externally visible colored zone 4. It should be appreciated that the colored zone 4 is concealed behind the sweat-absorbent sheet 51 and therefore eliminated in FIG. 2.

A lower end 50a and an upper end 50b of the rectangular sweat-absorbent sheet 51 extend in the longitudinal direction thereof, i.e., in the transverse direction of the diaper 1a, and substantially in parallel to the rear lower edge 47a of the rear turnback 47. A dimension of the sweat-absorbent sheet 51 as measured in the transverse direction of the diaper 1a is larger than the corresponding dimension of the bodily fluid-absorbent structure 30 and same as or smaller than the corresponding dimension of the rear turnback 47. FIG. 2 shows the exemplary embodiment in which the sweat-absorbent sheet 51 fully extends between the transversely opposite lateral edges 8a, 8a. A dimension of the sweat-absorbent sheet 51 as measured between the lower end 50a and the upper end 50b thereof is smaller than a dimension of the rear turnback 47 as measured between the rear lower edge 47a and a rear upper edge 47b thereof.

The sweat-absorbent sheet 51 comprises a top layer and bottom layer each formed by air-permeable non-woven fabric of polyester fiber having a basis weight of 25 g/cm$^2$ and a middle layer formed by moisture-absorbent tissue paper impregnated with antimicrobial agent and having a basis weight of 2-0 g/cm$^2$. After these three layers may be stacked on one another, this stack is subjected to impact of high-pressure to tangle component fibers of these layers and thereby to obtain the sweat-absorbent sheet 51. When the sweat-absorbent sheet 51 of such construction comes in contact with the wearer's skin, sweat permeates, disperses from the top layer into the middle layer and can be held therein. In this way, uncomfortable wet feeling is eliminated and the wearer experiences pleasant cooling sensation.

The antimicrobial agent with which the middle layer of the sweat-absorbent sheet 51 functions to inhibit proliferation of microbes such as *Staphylococcus* epiermidis due to sweat and thereby to inhibit development of heat rash due to such microbes. Such antimicrobial agent may be selected from a group of quaternary ammonium salts such as alkylpyridinium salt, alkylammonium salt, alkylbenzildimethyl ammonium salt (benzalkonium chloride), dialkyldimethyl ammonium salt and benzethonium chloride. Such antimicrobial agent may include additive, for example, catechin, if desired.

The adhesive region 61 in which the sweat-absorbent sheet 51 is bonded to the rear turnback 47 is provided so as to be spaced inward from an outer peripheral edge 58 of the sweat-absorbent sheet 51 and implemented as small dots of hot melt adhesive 57 distributed at a rate of 1 to 20 dots/cm$^2$. Between the outer peripheral edge 58 and the adhesive region 61 of the sweat-absorbent sheet 51, a non-adhesive region 62 is left, in which the sweat-absorbent sheet 51 is free from the rear turnback 47. As will be apparent from FIG. 2, the outer peripheral edge 58 of the sweat-absorbent sheet 51 includes the lower end 50a and the upper end 50b.

The colored zone 4 is defined by or within the adhesive region 61 so as to extend outside the rear end 42 of the bodily fluid-absorbent structure 30. In other words, the colored zone is spaced from the outer peripheral edge 58 of the sweat-absorbent sheet 51 and is provided in a zone of the sheet assembly 10 constituting the diaper 1a in which the liquid-absorbent material 31 containing fluff pulp is not present.

Figure 3:
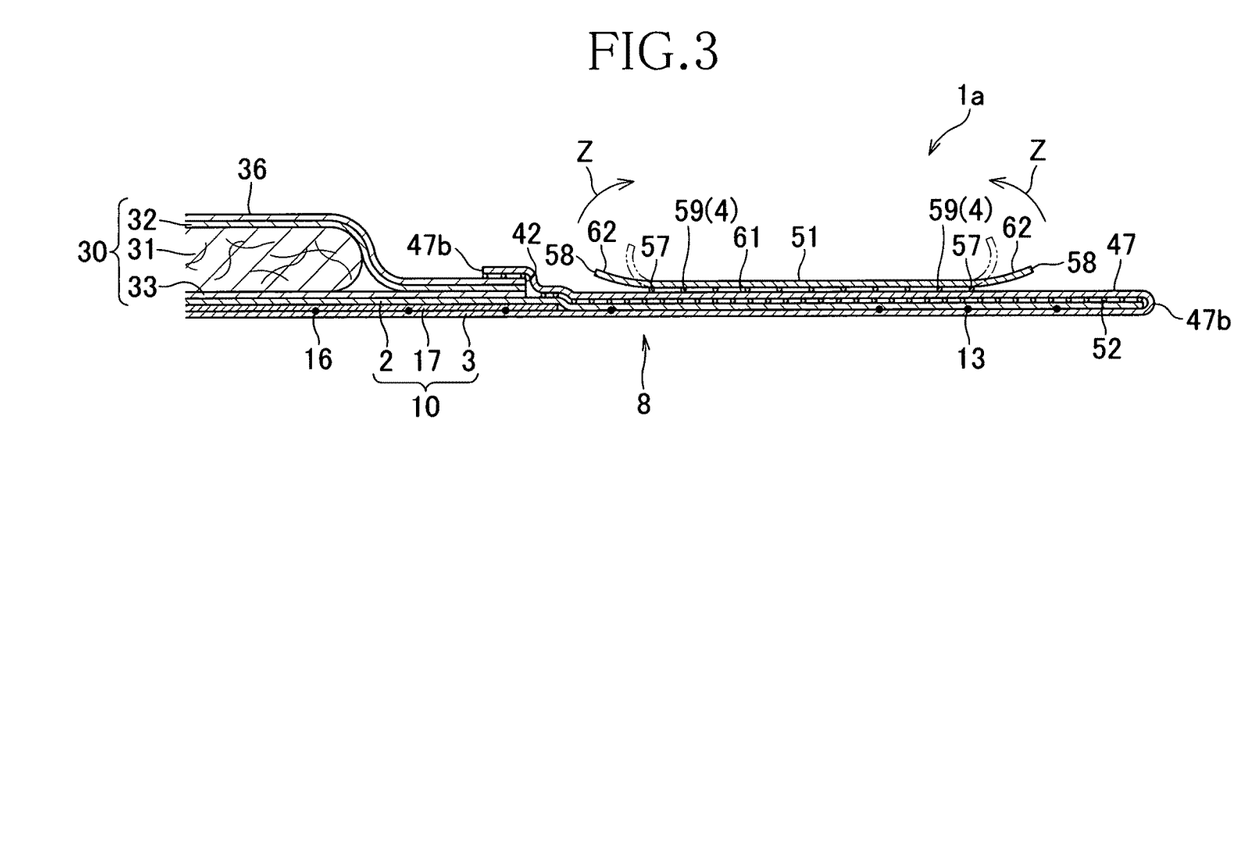
FIG. 3 is a sectional view taken along a line in FIG. 2.

FIG. 3 is a sectional view taken along a line in FIG. 2. The sweat-absorbent sheet 51 is bonded to the turnback 47 of the back-sheet 3 by the intermediary of the adhesive region 61 so as to be kept in contact with the wearer's skin and includes the non-adhesive region 62 between the adhesive region 61 and the outer peripheral edge 58 of the sweat-absorbent sheet 61.

The colored zone 4 is defined by a plurality of ink dots 59 printed on the sweat-absorbent sheet 51 in the same regions as the adhesive region 61 so as to be sandwiched between the sweat-absorbent sheet 51 and the turnback 47. These ink dots 4 are arranged within a zone spaced from the rear end 42 of the bodily fluid-absorbent structure 30.

As will be apparent from FIG. 3, the colored zone 4 is visible from the side of the diaper 1a facing the wearer's skin through the sweat-absorbent sheet 51 formed by non-woven fabric. In other words, the wearer or the helper can make sure that the diaper 1a is of the type provided with the sweat-absorbent sheet 51 and determine the position of this sweat-absorbent sheet 51 merely by opening the diaper 1a in the pants-shape adapted to be put on the wearer's body. Thus it is easily possible to position the sweat-absorbent sheet 51 properly on the rear waist region of the wearer.

The sweat-absorbent sheet 51 is provided in the region of the diaper 1a free from the presence of the liquid-absorbent material 31 including the fluff pulp. With such arrangement, the colored zone 4 is easily visible through the top-sheet 2 and the turnback 47 of the back-sheet 3 and there is no anxiety that the colored zone 4 might be shielded by the liquid-absorbent material 31 which is impenetrable to light. The wearer or the helper is allowed thereby to eliminate the need for opening the diaper 1a in the pants-shape in order to make sure that the diaper 1a is of the type provided with the sweat-absorbent sheet 51.

The colored zone 4 is provided so as to be sandwiched between the sweat-absorbent sheet 51 and the turnback 47 of the back-sheet 3 and thereby covered with the sweat-absorbent sheet 51. With this arrangement, there is no possibility that the colored zone 4 might come in direct contact with the wearer's skin and the wearer's skin might be contaminated with a quantity of ink 51 rubbed off from the colored zone 4.

In addition, the colored zone 4 is provided within the adhesive region 61, leaving the non-adhesive region 62. Even if the force tending to curl up the sweat-absorbent sheet 51 is exerted thereupon in the course of putting the diaper 1a on the wearer's body or due to movement of the wearer, the non-adhesive region 62 is sufficiently deformable to be curled up in first as indicated by an arrow Z in FIG. 3 and thereby to restrict a possibility that the sweat-absorbent sheet 51 might be curled up over the unacceptable range. Consequentially, there is no anxiety that the colored zone 4 might be exposed due to curling up of the sweat-absorbent sheet 51 over the unacceptable range and the wearer's skin might be contaminated with ink rubbed off from the colored zone 4. A width dimension of such non-adhesive region 62, i.e., a distance between the outer peripheral edge 58 of the sweat-absorbent sheet 51 and the adhesive region 61 is at least 1 mm or larger, preferably 3 mm or larger.

Ink 59 used to form the colored zone 4 is not specified and may be appropriately selected from a group commonly used in the relevant technical field depending on the materials of the sweat-absorbent sheet 51 and the sheet assembly 10. To improve the visibility of the colored zone 4, it is preferred to enhance a differential light value between the colored zone 4 and the sweat-absorbent sheet 51 and the turnback 47 of the back-sheet 3 both covering the colored zone 4. In general, the absorbent article is typically made using white non-woven fabric. If the white non-woven fabric used as stock material for the absorbent article is of poor see-through, printing ink of lower light value, for example, black, blue or green printing ink may be used to enhance the differential light value with respect to this non-woven fabric and thereby to improve the visibility of the colored zone 4.

Figure 4:
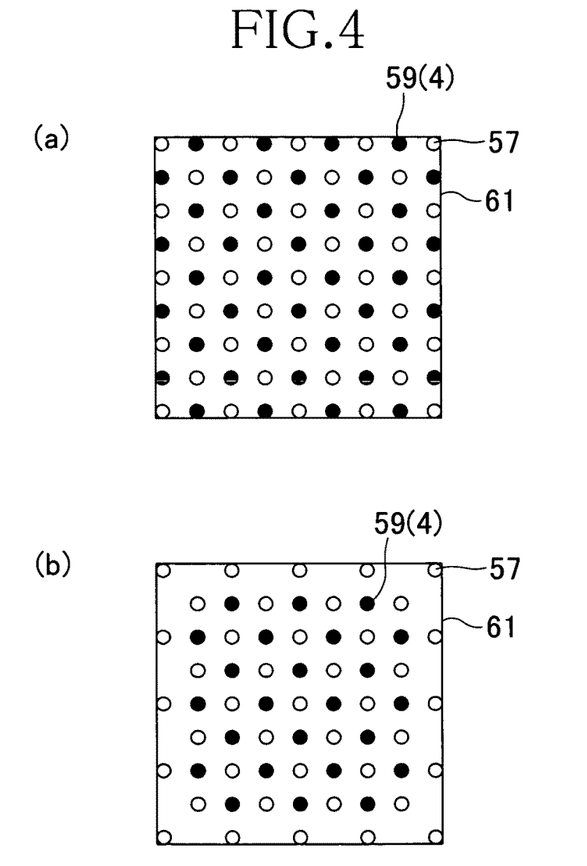
FIG. 4 is a diagram illustrating a pattern in which the adhesive region is printed with ink.

According to one exemplary embodiment of the colored zone 4 provided within the adhesive region 61, the dots of hot melt adhesive 57 and the dots of ink 59 may be arranged in alternate shifts to present a printing pattern of ink 59 as schematically illustrated by FIG. 4(a). By printing the sweat-absorbent sheet with the dots of ink 59 in this manner, it is possible to restrict an increase in stiffness of the sweat-absorbent sheet 51 compared to the case in which the sweat-absorbent sheet 51 is printed with continuous lines of ink 59 and thereby to maintain comfortable drape of the non-woven fabric constituting the sweat-absorbent sheet 51.

To keep a desired air-permeability of the sweat-absorbent sheet 51, a total coated area of ink 59 is preferably limited to 30% or less with respect to a total area of the adhesive region 61. To reduce the total coated area of ink 59 as effectively as possible, a central zone of the adhesive region 61 as viewed in FIG. 4(a) may be left not printed with ink 59. Alternatively, it is also possible to replace the filled dots of ink 59 by small rings each defined by an outer diameter of 1.0 mm and an inner diameter of 0.6 mm or less encircling a non-printed area.

Even if the sweat-absorbent sheet 51 is printed with ink 59 in a pattern of the small rings each having the inner diameter of 0.6 mm or less encircling the non-printed area as has been described above, it is difficult for the naked eye to distinguish the small rings from the filled dots of ink 59. This is for the reason that the outline of the small ring necessarily blurs through the non-woven fabric and the non-printed area can not be visually recognized. Taking account of this, the sweat-absorbent sheet 51 may be advantageously printed with ink 59 in the pattern of small rings distributed in the given region to reduce the total printed area while the same level of visibility as the case of printing in the pattern of filled dots. In this way, it is possible to obtain the sweat-absorbent sheet 51 exhibiting high air-permeability.

Alternatively, the sweat-absorbent sheet 51 may be printed with ink 59 inside the adhesive region 61 as illustrated by FIG. 4(b) to provide the colored zone 4 inside the adhesive region 61. With this arrangement, the portion of the sweat-absorbent sheet 51 extending outward beyond the colored zone 4 is sealed by the adhesive region 61 and thereby effectively protects the wearer's skin from being contaminated with ink 59 even if the sweat-absorbent sheet 51 is partially curled up. It should be appreciated that the portions of the sweat-absorbent sheet 51 and/or the back-sheet 3 or the other sheets constituting the sheet assembly 10 which respectively correspond to the adhesive region 61 have been previously printed with ink 59.

It is also possible to use hot melt adhesive containing an appropriate pigment to form the colored zone 4. With such arrangement, the wearer's skin can be effectively protected from contamination and the step of printing with ink 59 can be eliminated since the pigment is reliably sealed in the hot melt adhesive.

Figure 5:
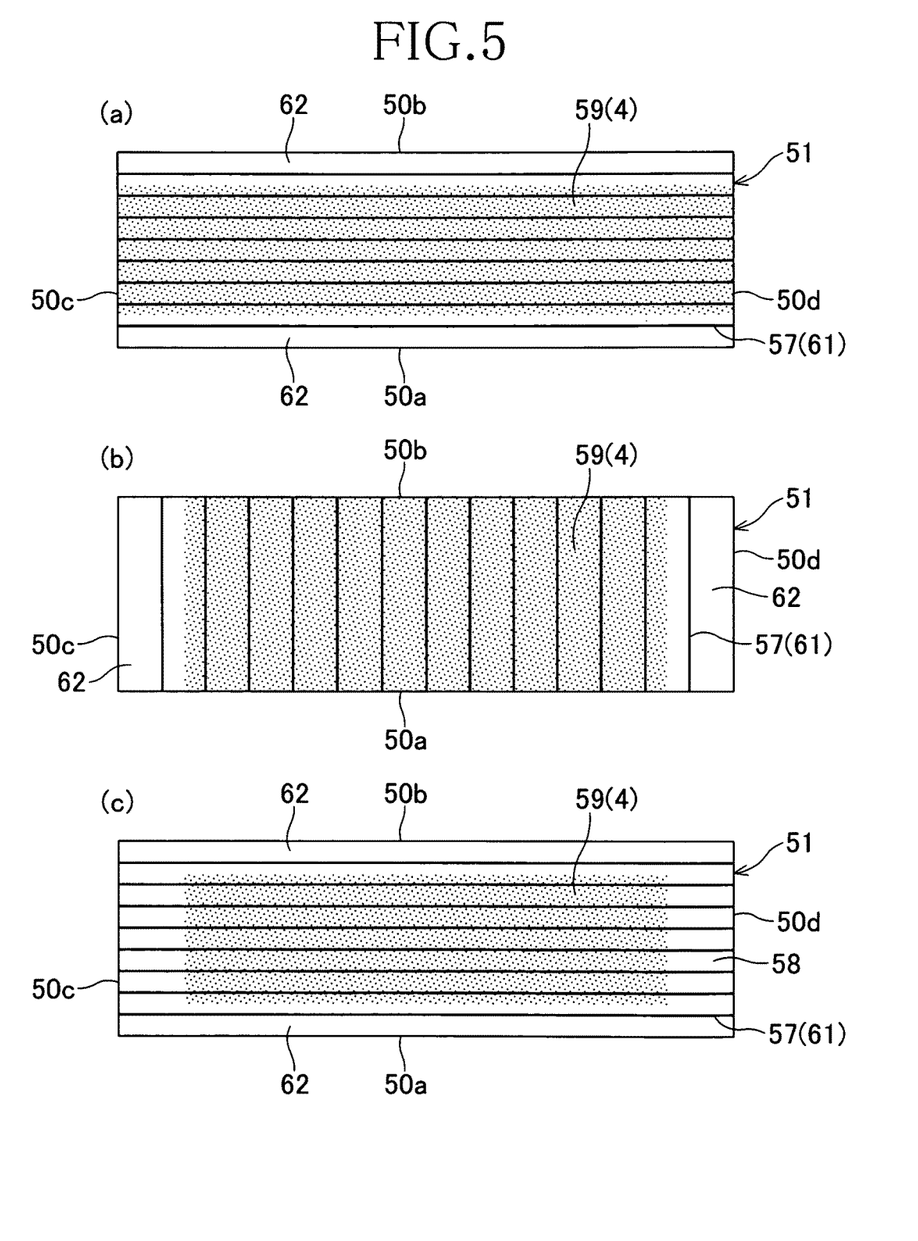
FIG. 5 is a diagram illustrating a pattern in which the functional sheet is printed with ink.

Patterns in which the sweat-absorbent sheet 51 serving as the functional sheet may be printed with ink 59 are schematically illustrated by FIG. 5(a)-FIG. 5(c). While the invention will be described hereinafter with respect to the case in which the sweat-absorbent sheet 51 is printed with ink 59, it is also possible to print the sheet assembly 10 with ink 59. The colored zone 4 may be formed by printing the rectangular sweat-absorbent sheet 51 with ink 59 in the pattern of dots so that the colored zone 4 is spaced from the lower end 50a and the upper end 50b and comes in contact with the transversely opposite lateral edges 50c, 50d of the rectangular sweat-absorbent sheet 51 as illustrated by FIG. 5(a). Alternatively, the colored zone 4 may be formed by printing the rectangular sweat-absorbent sheet 51 with ink 59 in the pattern of dots so that the colored zone 4 comes in contact with the lower end 50a and the upper end 50b and is spaced from the transversely opposite lateral edges 50c, 50d of the rectangular sweat-absorbent sheet 51 as illustrated by FIG. 5(b).

The sweat-absorbent sheet 51 is coated with hot melt adhesive 57 in pattern of stripes extending in the longitudinal direction of the sheet 51 to form the adhesive region 61 fully extending between the transversely opposite lateral edges 50c, 50d so as to leave the non-adhesive regions 62 extending along the lower end 50a and the upper end 50b as illustrated by FIG. 5(a). Alternatively, the sweat-absorbent sheet 51 may be coated with hot melt adhesive 57 in pattern of stripes extending in the vertical direction orthogonal to the longitudinal direction so as to leave the non-adhesive regions 62 extending along the lateral sides 50c, 50d as illustrated by FIG. 5(b). As seen in both cases, the non-adhesive regions 62 may be left not along the complete outer periphery but along a part of the outer periphery of the sweat-absorbent sheet 51.

It should be noted here that the sweat-absorbent sheet 51 attached to the diaper 1a so that the longitudinal direction thereof may be parallel to the transverse direction of the diaper 1a, the sweat-absorbent sheet 51 is apt to be curled up in the vertical direction due to movement of the wearer's body. To overcome such problem, the sweat-absorbent sheet 51 may be coated with hot melt adhesive 57 extending in the vertical direction as illustrated by FIG. 5(b) to leave the non-adhesive regions 61 extending in vertical direction from the lower end 50a to the upper end 50b. In this way, undesirable curling up of the sweat-absorbent sheet 51 can be reliably restricted even if the wearer's body moves.

According to another exemplary embodiment, the sweat-absorbent sheet 51 may be printed with ink 59 in the pattern of dots distributed in the region spaced from the lower end 50a, the upper end 50b and the transversely opposite lateral edges 50c, 50d of the sweat-absorbent sheet 51. In this case, the sweat-absorbent sheet 51 may be coated with hot melt adhesive 57 in stripe-pattern extending in the longitudinal direction or in the vertical direction of the sweat-absorbent sheet 51 as illustrated. In each case, it is essential to print the sweat-absorbent sheet 51 with ink 59 in the same region as the adhesive region 61 to be coated with hot melt adhesive 57 or within this adhesive region 61.

As has previously been described, the sweat-absorbent sheet 51 is implemented in the form of the laminate comprising the top and bottom layers formed by non-woven fabric of polyester fiber and the middle layer formed by tissue paper entangled together under impact of high pressure water stream.

Figure 6:
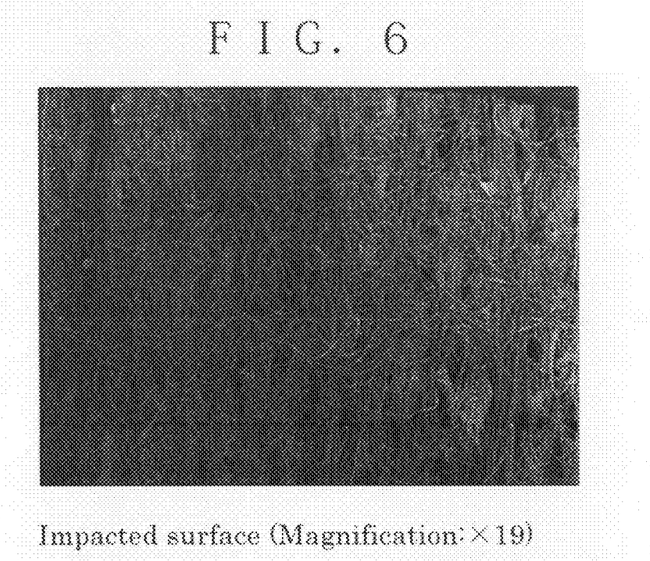
FIG. 6 is a SEM photograph of the surface of the sweat-absorbent sheet directly subjected to impact of high-pressure water stream.
Figure 7:
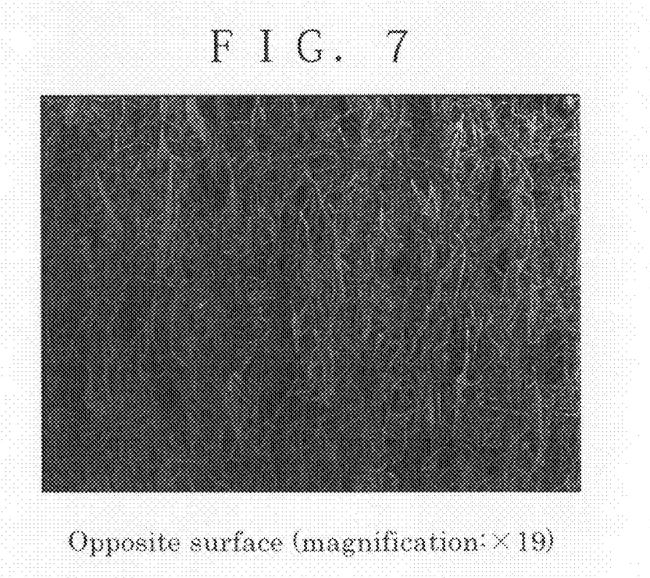
FIG. 7 is a SEM photograph of the surface opposite to the surface directly subjected to impact of high-pressure water stream.

The surface of the sweat-absorbent sheet 51 directly subjected to impact of high pressure water stream (referred to hereinafter as the impacted surface) and the surface opposite to the impacted surface (referred to hereinafter as the opposite surface) of the sweat-absorbent sheet 51 were compared to each other using Scanning Electron Microscope (SEM) of JSM-5800 Model manufactured by JEOL Ltd. It was found from this microscopic comparison that many of the component fibers on the impacted surface are oriented in one direction with relatively few intersections (See FIG. 6). In contrast with this, the component fibers on the opposite surface were oriented under a bouncing effect of high pressure water stream at the moment of impacting of high pressure water stream rather at random than on the impacted surface and the number of intersections was correspondingly increased (See FIG. 7).

Fewer intersections of the component fibers on the impacted surface make the impacted surface smoother than the opposite surface.

In other words, the opposite surface of the sweat-absorbent sheet 51 may be printed with ink 59 and thereby the colored zone 4 may be formed to ensure that the colored zone 4 is easily visible when the colored zone 4 is observed through the smooth impacted surface from the side of the sweat-absorbent sheet 51 facing the wearer's skin. In addition, the smooth impacted surface lying on the side facing the wearer's skin serves to improve close contact of the sweat-absorbent sheet 51 with the wearer's skin and thereby to improve efficiency of sweat-absorbent and antimicrobial function for the wearer's skin.

Figure 8:
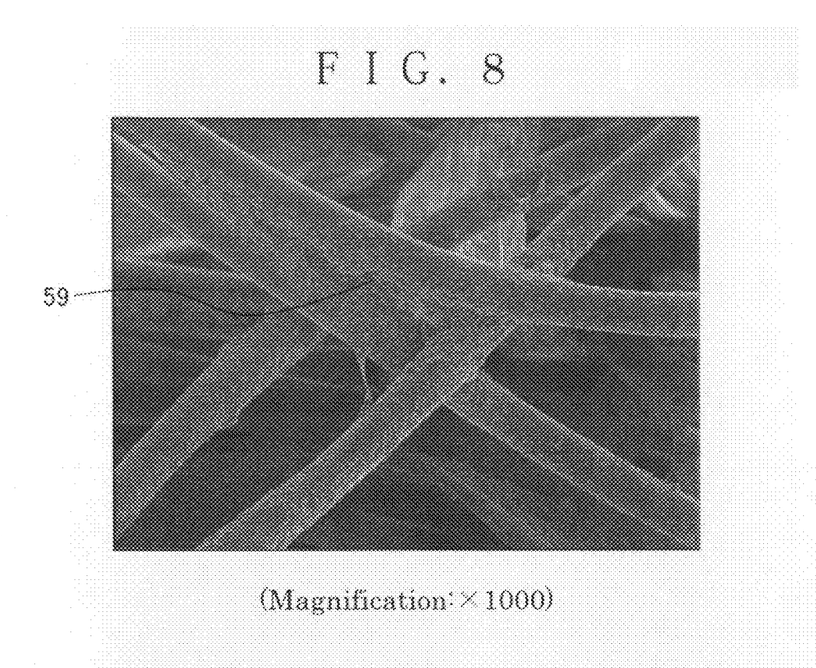
FIG. 8 is a SEM photograph of fibers' crossover points printed with ink.
Figure 9:
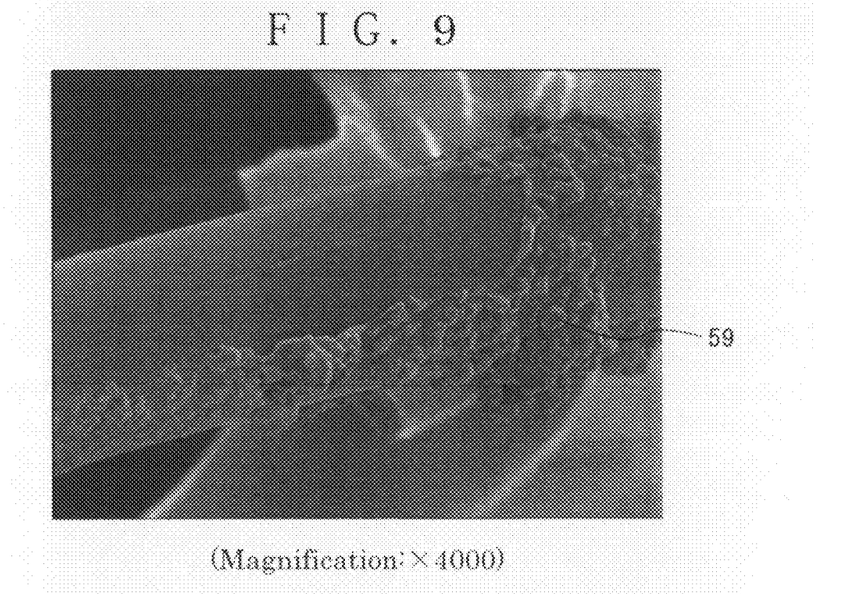
FIG. 9 is a SEM photograph of ink attached to a single fiber.

From SEM observation of the sweat-absorbent sheet 51 printed with ink 59, it was found that a quantity of ink 59 clings, at each of the intersections of the component fibers, in form of film extending between each pair of the adjacent component fibers (See FIG. 8) over an area larger than an area over which the same quantity of ink 59 clings to the single component fiber (See FIG. 9). In other words, the same quantity of ink 59 is able to color the sweat-absorbent sheet 51 over the area larger at each of the intersections than on the single fiber. In consideration of this, the opposite surface including many intersections of the component fibers may be printed with the same quantity of ink 59 to form the colored zone 4 presenting relatively high visibility.

As will be obvious from the description given heretofore, the sweat-absorbent sheet 51 is preferably formed by subjecting the laminate comprising the liquid-absorbent middle layer and the top and bottom layers both being air-permeable and liquid-pervious and formed by the air-permeable and liquid-pervious fibrous non-woven fabric made of synthetic resin to the impact of high pressure water stream directed from the top layer toward the bottom layer so as to intertangle the component fibers of the laminate. The bottom layer side (the opposite surface) of the sweat-absorbent sheet 51 formed in this manner may be provided with the colored zone 4 and the top layer (the impacted surface) may be bonded to the sheet assembly 10 so as to be kept in contact with the wearer's skin to improve visibility of the colored zone 4 and close contact of the sweat-absorbent sheet 51 with the wearer's skin.

While the exemplary embodiments have been described above, the present invention is not limited to these embodiments and details thereof may be modified in various manners without departing from the scope of the invention.

For example, while the sweat-absorbent sheet 51 has been described to comprise tissue paper sandwiched a pair of non-woven fabric layers made of polyester fiber, the invention is not limited to such embodiment so far as the sweat-absorbent sheet 51 is of trilaminar structure consisting of the liquid-absorbent middle layer reinforced by the top and bottom layers both made of air-permeable and liquid-pervious non-woven fabric of synthetic resin fiber or film. It is possible therefore to use hydrophilic fiber containing cellulose, for example, rayon, cotton or pulp as stock material for the middle layer. As stock material of the top layer and the bottom layer, it is possible to use air-permeable and liquid-pervious fibrous non-woven fabric or film, for example, of polyethylene or polypropylene.

When non-woven fabric is used for the top layer and the bottom layer, two or more types of fibers may be mixed together. For example, polyester fiber modified to become hydrophilic may be mixed to improve the liquid-pervious property of the sweat-absorbent sheet 51. To modify polyester fiber to become hydrophilic, for example, polyethylene glycol may be blended with polyester or graft polymerized with polyester to achieve desired modification.

While the sheet assembly 10 has been described to comprise the top-sheet 2, the back-sheet 3 and the leak-barrier sheet 17 as basic components, it is possible to increase the number of component sheets constituting the sheet assembly 10, for example, by bisecting the top-sheet 2. Alternatively, the top-sheet 2 and the back-sheet 3 may be put flat together and bonded to each other along the front edge 7b and the rear edge 8b without folding back the back-sheet 3. Ink 59 forming the colored zone 4 may contain ingredients other than pigment, for example, appropriate agent having solvatochromic property to water such as cobalt chloride(II).

While the exemplary embodiment has been described above in which the colored zone 4 is formed so as to be spaced from the rear end 42 of the bodily fluid-absorbent structure 30, the position relationship between the colored zone 4 and the bodily fluid-absorbent structure 30 is not limited to such exemplary embodiment. For example, the colored zone 4 may partially overlap the tissue paper layers 32, 33 constituting the bodily fluid-absorbent structure 30 or partially overlap the liquid-absorbent material 31.

In other words, the colored zone 4 may be formed at the position corresponding to the position of the functional sheet (i.e., sweat-absorbent sheet 51) and sandwiched between the functional sheet and the sheet assembly 10 so as to be externally visible. Position and size of the functional sheet relative to the bodily fluid-absorbent structure 30 as well as to the liquid-absorbent material 31 may be appropriately selected.

The invention claimed is:

1. An absorbent article comprising:
   a crotch region;
   a front waist region extending forward from the crotch region;
   a rear waist region extending rearward from the crotch region;
   a sheet assembly comprising:
     a top-sheet;
     a back-sheet; and
     a leak-barrier sheet;
   a functional sheet comprising an antimicrobial sweat-absorbent sheet and having a size smaller than that of said sheet assembly; and a bodily fluid-absorbent structure wherein said functional sheet and said bodily fluid-absorbent structure are attached to said sheet assembly, a portion of said back-sheet is folded back along a rear edge onto a side of said rear waist region on which said bodily fluid-absorbent structure is attached to define a rear turnback, said rear turnback of said back sheet is bonded to said topsheet, and said functional sheet is put flat with and bonded to said rear turnback so as to be kept in contact with a wear's skin when the absorbent article is used; and an externally visible colored zone is provided between said functional sheet and said rear turnback.

2. The absorbent article according to claim 1, wherein:

said functional sheet is bonded to said sheet assembly by the intermediary of an adhesive region;

said adhesive region is provided so as to be spaced inward from an outer peripheral edge of said functional sheet; and said colored zone is provided in a same region as said adhesive region or within said adhesive region.

3. The absorbent article according to claim 1, wherein said colored zone is formed by at least one of:

ink with which said functional sheet is printed;

ink with which said sheet assembly is printed; and hot melt adhesive used to bond said functional sheet to said sheet assembly and containing a pigment.

4. The absorbent article according to claim 1, wherein:

said bodily fluid-absorbent structure includes a liquid-absorbent material at least containing fluff pulp; and said colored zone is provided in a region of said sheet assembly in which said liquid-absorbent material is not present.

5. The absorbent article according to claim 3, wherein:

said bodily fluid-absorbent structure includes a liquid-absorbent material at least containing fluff pulp; and said colored zone is provided in a region of said sheet assembly in which said liquid-absorbent material is not present.

6. The absorbent article according to claim 2, wherein said colored zone is formed by at least one of:

ink with which said functional sheet is printed;

ink with which said sheet assembly is printed; and hot melt adhesive used to bond said functional sheet to said sheet assembly and containing a pigment.

7. The absorbent article according to claim 6, wherein:

said bodily fluid-absorbent structure includes a liquid-absorbent material at least containing fluff pulp; and said colored zone is provided in a region of said sheet assembly in which said liquid-absorbent material is not present.

8. The absorbent article according to claim 2, wherein:

said bodily fluid-absorbent structure includes a liquid-absorbent material at least containing fluff pulp; and said colored zone is provided in a region of said sheet assembly in which said liquid-absorbent material is not present.

* * * * *

UNITED STATES PATENT AND TRADEMARK OFFICE
CERTIFICATE OF CORRECTION

PATENT NO.       : 8,486,036 B2                                           Page 1 of 1
APPLICATION NO. : 12/449319
DATED            : July 16, 2013
INVENTOR(S)      : Tange et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 974 days.

Signed and Sealed this
Eighth Day of September, 2015

Michelle K. Lee
*Director of the United States Patent and Trademark Office*